US009340560B2

(12) United States Patent
Bade et al.

(10) Patent No.: US 9,340,560 B2
(45) Date of Patent: May 17, 2016

(54) PROCESS FOR ESTERIFYING SILICON-HALOGEN COMPOUNDS IN A COLUMN AND APPARATUS SUITABLE THEREFOR

(71) Applicants: Stefan Bade, Michelbach le Haut (FR); Norbert Schladerbeck, Kelkheim (DE); Andre Nehls, Schwoerstadt (DE)

(72) Inventors: Stefan Bade, Michelbach le Haut (FR); Norbert Schladerbeck, Kelkheim (DE); Andre Nehls, Schwoerstadt (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/767,651

(22) PCT Filed: Jan. 16, 2014

(86) PCT No.: PCT/EP2014/050835
§ 371 (c)(1),
(2) Date: Aug. 13, 2015

(87) PCT Pub. No.: WO2014/124776
PCT Pub. Date: Aug. 21, 2014

(65) Prior Publication Data
US 2015/0353586 A1      Dec. 10, 2015

(30) Foreign Application Priority Data

Feb. 13, 2013   (DE) .......................... 10 2013 202 325

(51) Int. Cl.
| | |
|---|---|
| *C07F 7/18* | (2006.01) |
| *C07F 7/04* | (2006.01) |
| *B01J 19/24* | (2006.01) |
| *C07F 7/08* | (2006.01) |

(52) U.S. Cl.
CPC ................. *C07F 7/045* (2013.01); *B01J 19/24* (2013.01); *C07F 7/18* (2013.01); *C07F 7/188* (2013.01); *C07F 7/1836* (2013.01); *B01J 2219/00076* (2013.01); *B01J 2219/24* (2013.01); *C07F 7/04* (2013.01); *C07F 7/08* (2013.01)

(58) Field of Classification Search
CPC ................. C07F 7/18; C07F 7/04; C07F 7/08
USPC .......................................... 556/471, 445, 446
See application file for complete search history.

(56) References Cited

U.S. PATENT DOCUMENTS

| | | | |
|---|---|---|---|
| 3,792,071 A | 2/1974 | Nitzsche et al. | |
| 4,642,363 A | 2/1987 | Groh et al. | |
| 6,150,550 A | 11/2000 | Bade et al. | |
| 7,507,850 B2 | 3/2009 | Müh et al. | |

OTHER PUBLICATIONS

International Search Report Issued Apr. 24, 2014 in PCT/EP2014/050835 Filed Jan. 16, 2014.

*Primary Examiner* — Elvis O Price
(74) *Attorney, Agent, or Firm* — Oblon, McClelland, Maier & Neustadt, L.L.P.

(57) ABSTRACT

What is described is a process for continuously esterifying halosilanes of the formula I with alcohols of the formula II to give silane esters of the formula III in a single column (1)

Figure 1:
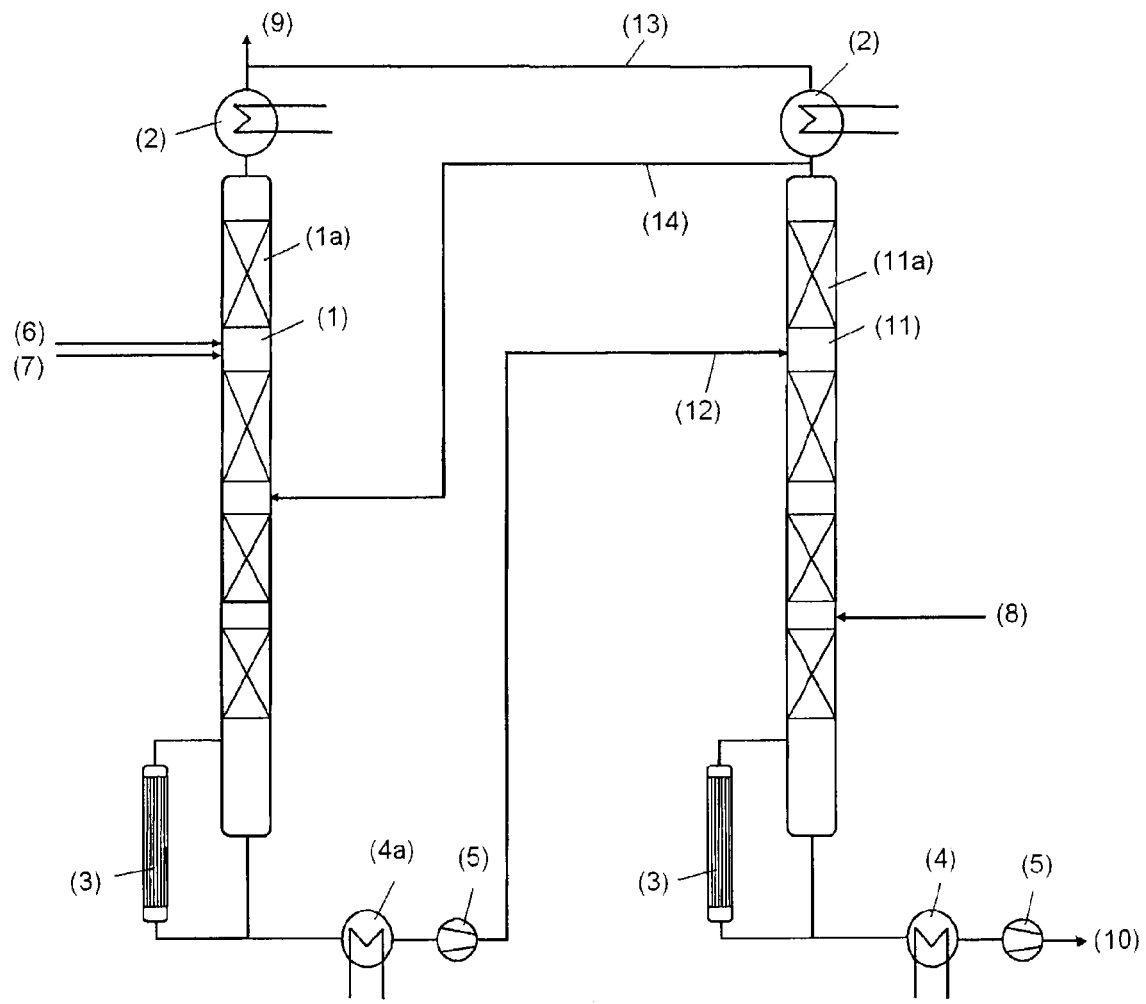

$$R^1_a SiHal_b \qquad (I)$$
$$R^2{-}(OH) \qquad (II)$$
$$R^1_a S{-}(OR^2)_b \qquad (III)$$

in which $R^1$ is hydrogen or a monovalent organic radical, where any two $R^1$ radicals within a molecule may be different within the scope of the given definitions,
Hal is a halogen atom, a plurality of Hal atoms within a molecule may be different within the scope of the given definitions, $R^2$ is a monovalent organic radical, a and b are integers from 0 to 4 and the sum total of a and b is 4, comprising the measures of:
i) feeding the total amount of the halosilane of the formula I required for the reaction in liquid form through line (6) into the upper third of the column (1),
ii) feeding at least 60% by weight of the alcohol of the formula II required for the reaction in liquid form through line (7) into the upper third of the column (1),
iii) feeding the remainder of the alcohol of the formula II required for the reaction in liquid form through line (8) into the lower third of the column (1),
iv) conducting the reaction of the halosilane of the formula I with the alcohol of the formula II to give the silane ester of the formula III in the interior of the column (1), the temperature in the interior of the column (1) between line (7) and line (8) being below the boiling temperature of the alcohol of the formula II,
v) removing the hydrogen chloride formed in the reaction via the top of the column (1), and
vi) removing the esterification product of the formula III formed in the reaction from the bottom of the column (1).
The invention also relates to a column (1) for continuously esterifying halosilanes of the above-described formula I with alcohols of the formula II to give silane esters of the formula III, comprising the following elements:
A) line (6) which opens into the upper third of the column (1) and which serves to feed in the halosilane of the formula I,
B) line (7) which opens into the upper third of the column (1) and which serves to feed in a portion of the alcohol of the formula II required for the reaction,
C) line (8) which opens into the lower third of the column (1) and which serves to feed in the remaining portion of the alcohol required for the reaction,
D) circulation evaporator (3) which is mounted in the lower third of the column and heats the bottom product present in the column (1),
E) line (9) for removing the hydrogen halide formed in the reaction via the top of the column (1), and
F) line (10) for removing the esterification product of the formula III formed in the reaction from the bottom of the column (1).
The process described allows the preparation of silane esters of the formula III with high selectivity.

16 Claims, 2 Drawing Sheets

PROCESS FOR ESTERIFYING SILICON-HALOGEN COMPOUNDS IN A COLUMN AND APPARATUS SUITABLE THEREFOR

The present invention relates to an improved process for continuously preparing (organo)silane esters or silicic esters in a single reactive distillation column, and to a column suitable for that purpose.

EP 0 107 765 A2 discloses the reaction of chlorosilanes with alcohols to give alkoxysilanes in a combination of reactor and a column connected thereto.

EP 0 924 215 A2 describes a process for preparing alkoxysilanes by reacting organohalosilanes with alcohols by means of a reactive extraction. For this purpose, the organohalosilane is dissolved in a liquid with which the alcohol is immiscible, and the two liquids are contacted with one another.

EP 0 650 968 A1 describes a continuous process for preparing aqueous alkali metal alkylsiliconate solutions. For this purpose, in a first stage, organotrichlorosilane and alcohol are converted in a reactor. In a second stage, the reaction mixture from the first stage is reacted further in a column with further alcohol in countercurrent and, in a third stage, the esterification product from the second stage is reacted with alkali metal hydroxide solution in a mixing reactor to give the end product.

DE 30 00 782 A1 discloses a continuous process for preparing polysiloxanes having SiOC groups. The process comprises the reaction of chlorosilanes with alcohols in a column provided with a reflux condenser at elevated temperature. Connected upstream of this is a first reactor, for example a stirred tank or a tubular reactor, in which a liquid reaction mixture is produced from the reactants. This mixture is introduced at the top of a column. Also introduced at the lower end of the column is gaseous alcohol, in order to complete the reaction with the chlorosilane. The reaction product is drawn off at the lower end of the column.

EP 1 205 505 A2 describes a continuous process for preparing organoalkoxysilanes. The process is conducted in two process stages. The first process stage can be executed in a stirred tank or a reaction column, while the second process stage is executed in a reactive distillation column which is operated at a bottom temperature of 50 to 200° C. The reaction of organochlorosilane with alcohol and water in the first process stage is effected at temperatures between 0 and 150° C. The hydrogen chloride which forms is removed from the system and the crude product which forms is transferred into the second process stage after a mean residence time of 0.5 to 180 minutes.

EP 1 686 132 A1 describes a continuous process for preparing SiOC-containing compounds, for example alkoxysilanes or alkoxy-rich silicone resins. The process is conducted in two reaction units consisting of columns. Upstream of the first column is provided a preliminary reactor in which a chlorosilane is reacted with alcohol and optionally with water to give a reaction mixture which is conducted into the first reaction unit.

In the esterification of halosilanes with alcohols, it is nowadays customary to employ a two-column methodology, wherein a reactor column and a forerun column are used. In the reactor column, chlorosilane and alcohol are fed in in the middle. The hydrogen chloride formed in the reaction of these compounds is drawn off via the top of the column. The crude product obtained in the reaction is withdrawn from the bottom of the reactor column using a condenser and a pump, and fed into the forerun column. The crude product is heated again therein, fresh alcohol is additionally fed in, and the fully reacted crude product is withdrawn from the bottom of the forerun column.

The complete reaction of organohalosilane and alcohol in one column is also already known. DE 2 061 189 A describes a process for continuously preparing alkoxy(poly)silanes. The process comprises the reaction of chlorosilanes with alcohols and optionally water in a column which is kept at elevated temperature and has been provided with a reflux condenser. The chlorosilane is fed in at the top of the column, and evaporated alcohol in the lower third of the column. The reaction product is drawn off from the column below the feed for the alcohol. The temperatures in the interior of the column are adjusted such that boiling excess alcohol is always present at the top of the column during the reaction. The column is thus generally operated at elevated temperature. The previously known process is thus operated above the boiling point of the alcohol in question.

Finally, DE 34 31 839 A1 discloses a process for preparing trialkoxysilanes by reacting alkyltrihalosilanes with alcohols, in which the alcohol is added to the trialkoxysilane which is kept at or above boiling temperature, and wherein the reaction mixture, at least towards the end of the reaction, is kept under column distillation conditions, wherein the hydrogen chloride which forms is distilled off and then the alkyltrialkoxysilane is isolated. The reaction can be conducted in a combination of reactor and downstream column, but also in a single column.

Single column esterification is very advantageous over the combination of reactor and column. The pump between the reactor column and forerun column is dispensed with, as is the product cooler upstream of the pump. In addition, energy is saved because the crude product need no longer be cooled intermediately in the single column esterification in order subsequently to heat it up again. Furthermore, the capital costs are also of course lower than for a two-column or reactor column esterification.

However, the one-column esterification known to date is still in need of improvement. Thus, it has been found that the esterification with vaporous alcohol leads to a decrease in the theoretically possible conversion yield. Experiments have also shown that the feed point and the amount of the alcohol affect the selectivity of the reaction. Now an esterification process has been found which permits the conduct of the reaction in one column with high selectivity.

The present invention relates to a process for continuously esterifying halosilanes of the formula I with alcohols of the formula II to give silane esters of the formula III in a single column (1)

$$R^1_a SiHal_b \quad (I)$$

$$R^2-(OH) \quad (II)$$

$$R^1_a S-(OR^2)_b \quad (III)$$

in which $R^1$ is hydrogen or a monovalent organic radical, where any two $R^1$ radicals within a molecule may be different within the scope of the given definitions, Hal is a halogen atom, a plurality of Hal atoms within a molecule may be different within the scope of the given definitions, $R^2$ is a monovalent organic radical, a and b are integers from 0 to 4 and the sum total of a and b is 4.

The process according to the invention comprises the measures of:
i) feeding the total amount of the halosilane of the formula I required for the reaction in liquid form through line (6) into the upper third of the column (1),
ii) feeding at least 60% by weight of the alcohol of the formula II required for the reaction in liquid form through line (7) into the upper third of the column (1),
iii) feeding the remainder of the alcohol of the formula II required for the reaction in liquid form through line (8) into the lower third of the column (1),
iv) conducting the reaction of the halosilane of the formula I with the alcohol of the formula II to give the silane ester of the formula III in the interior of the column (1), the temperatures in the interior of the column (1) between line (7) and line (8) being below the boiling temperature of the alcohol of the formula II,
v) removing the hydrogen chloride formed in the reaction via the top of the column (1), and
vi) removing the esterification product of the formula III formed in the reaction from the bottom of the column (1).

In the process according to the invention, halosilane and alcohol are both fed into the column in liquid form. In the upper portion of the column, chlorosilane and alcohol are introduced at the same height, but separately from one another. In the lower portion of the column, there is a second feed of alcohol, also in liquid form, in order to adjust the product quality. The amount of alcohol in the upper portion is typically 70%-95% by weight, and in the lower portion typically 5%-30% by weight.

In the process according to the invention, halosilane and alcohol are fed in essentially in amounts required stoichiometrically. At the top of the column, typically only hydrogen chloride is removed, generally contaminated with small amounts of alcohol aerosols. Compared to the previously known one-column process, the temperature profile in the column is distinctly different in the process according to the invention. In the process according to the invention, there are high temperatures up to the boiling temperature of the product in the bottom of the column, while the temperature at the level of the feed points for halosilane and alcohols is below the boiling temperature of the alcohol, such that the alcohol is at least partly in liquid form between the feed points for the alcohol. Toward the top of the column, the temperature rises again and may have a maximum of the boiling temperature of the alcohol used.

One of the preferred embodiments to date in the esterification of halosilanes with alcohols was a two-column esterification system. The main conversion was effected in the first column, while the conversion was completed in the second column. The process gives high conversion levels and a good selectivity (low level of by-products and of residue), but the apparatus complexity and the energy balance are non-optimal. A further esterification system frequently used is the combination of an upstream stirred tank reactor for the main conversion and a downstream column as postreactor. Although this combination has the advantage of a high space-time yield, one disadvantage is the poorer product quality of the product formed, such that there is often a second downstream finishing column which is operated under reduced pressure.

The disadvantages of the existing esterification plants are summarized below:
high apparatus complexity
poor energy balance, because crude product is cooled down and heated up again
large space requirement in the setup of the plant
high maintenance costs because of the higher number of apparatuses
higher proportion of residue, and hence lower selectivity It has now been found that, surprisingly, the esterification reaction can be conducted with high selectivity in a single column as well, if the feed points for halosilane and alcohol are optimized. The process according to the invention also utilizes the known advantages of one-column esterification:
Distinctly reduced apparatus complexity: Compared to a two-column esterification, there is no need for connecting pipelines between the columns, for a product cooler in the bottoms output from the first column, for a crude product pump in the bottom of the first column, for a top condenser in the second column, for a circulation evaporator in the second column, for the second column itself and for all the measurement technology in the second column.
Improved energy balance: With the aid of a circulation evaporator, all the energy needed is introduced. There are only heat losses in one column, and no longer in two columns. There is no need to cool the crude product and reheat it in a second column. In the one-column esterification, only one product cooler in the bottom is used in order to cool down the product upstream of the pump and the downstream storage vessel.
Lower maintenance costs: Because of the smaller amount of apparatus used, the maintenance costs are distinctly reduced.
Less space required for a one-column esterification compared to a two-column esterification.
Fewer control circuits in the one-column esterification.
Less formation of residue in the one-column esterification because of the absence of the process steps of cooling and reheating.

The esterification reaction according to the invention can be described as follows:

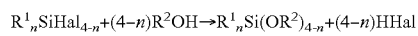

$$R^1{}_n SiHal_{4-n} + (4-n)R^2OH \rightarrow R^1{}_n Si(OR^2)_{4-n} + (4-n)HHal$$

where $R^1$, $R^2$ and Hal are each as defined above and n is an integer from 0 to 3.

The halosilane is esterified with alcohol, releasing gaseous hydrogen chloride ("HCl"). In order to separate the HCl, which has good solubility in the alcohol and in the product, mass transfer surface area has to be provided, and the heat for the desorption of the HCl has to be introduced.

According to the invention, this reaction is conducted in a reactive distillation. Here, the chemical reaction and the physical separation of the HCl are effected at the same time.

A particularly preferred reaction according to the invention is the reaction of vinyltrichlorosilane with methanol or with ethanol to give vinyltrimethoxysilane or vinyltriethoxysilane.

$R^1$ may be hydrogen or a monovalent organic radical. When two or more $R^1$ radicals are present in the molecule, these radicals may be different within the scope of the given definitions.

$R^2$ is a monovalent organic radical.

The organic radicals may be linear or branched alkyl, alkenyl, cycloalkyl, aryl, aralkyl and/or heterocyclyl. These may optionally be substituted, for example by alkyl, alkoxy, hydroxyl, amino, halogen or nitro. In the alkyl radicals, one or more carbon atoms not directly adjacent to one another may be replaced by oxygen or sulphur atoms or by imino groups.

Alkyl groups may be straight-chain or branched and typically have one to twenty carbon atoms. Preference is given to $C_1$-$C_6$-alkyl radicals. Examples of alkyl radicals are methyl, ethyl, n-propyl, isopropyl, n-butyl, sec-butyl, tert-butyl, n-pentyl and n-hexyl. Preference is given to methyl and ethyl. Substituted alkyl groups may, inter alia, be hydroxyalkyl groups, for example hydroxyethyl, hydroxypropyl and hydroxybutyl. Further preferred monovalent organic radicals for $R^2$ are methoxyethyl [$CH_3—O—(CH_2)_2—$] or ethoxyethyl [$CH_3—CH_2—O—CH_2—$], and also aminoethyl [$H_2N—(CH_2)_2—$].

Alkenyl groups may be straight-chain or branched and typically have two to twenty carbon atoms. Preference is given to $C_2$-$C_3$-alkenyl radicals. Alkenyl radicals may have one or more double bonds. When two or more double bonds are present, they are separated from one another at least by one single bond. Preferably, only one double bond is present. This is more preferably in the alpha position. Examples of alkenyl radicals are vinyl and allyl. Preference is given to vinyl.

Cycloalkyl groups generally have five to eight ring carbon atoms. Preference is given to cycloalkyl groups having six ring carbon atoms. Examples of cycloalkyl radicals are cyclopentyl, cyclohexyl and cycloheptyl. Preference is given to cyclohexyl.

Aryl groups may be mono- or polycyclic. Two or more cycles may be joined to one another via single bonds or via bridging groups, for example via —O—, —CO— or —CH$_2$— groups. Examples of aryl radicals are phenyl or naphthyl. Preference is given to phenyl. Aralkyl groups are monovalent organic radicals having an aryl group bonded covalently to an alkylene group and a bond on the alkylene radical to the rest of the molecule. Examples of aryl radicals are listed above. Alkylene radicals may be straight-chain or branched and typically have one to twenty carbon atoms. Preference is given to aralkyl radicals having $C_1$-$C_6$-alkylene radicals. One example of an aralkyl radical is benzyl.

Heterocyclyl groups are cyclic organic radicals having heteroatoms, for example oxygen, sulphur or nitrogen atoms, in the ring. Heterocyclyl groups generally have five to eight ring atoms, of which typically one to three ring atoms are heteroatoms. Preference is given to heterocyclyl groups having five or six ring atoms, which more preferably have one or two oxygen, sulphur or nitrogen atoms, where no two oxygen atoms are adjacent to one another.

"Hal" in the context of this description is understood to mean halogen atoms, i.e. fluorine, chlorine, bromine and iodine. Preference is given to chlorine and bromine, very particular preference to chlorine.

In a preferred process, compounds of the formula I in which $R^1$ is hydrogen and/or $C_1$-$C_6$-alkyl and/or vinyl, especially hydrogen, methyl, ethyl or vinyl, and in which $R^2$ is $C_1$-$C_6$-alkyl, especially methyl or ethyl, are used.

In a further preferred process, the amount of alcohol of the formula II fed in through line (7) is 70% to 95% by weight of the amount required for the reaction, and the remaining amount of the alcohol of the formula II required for the reaction is introduced in liquid form into the lower third of the column (1) through line (8).

More preferably, the compounds of the formulae I and II are fed into the middle of the column (1) through lines (6, 7, 8); at the column end, there is a 90° pipe bend directed downward.

Preference is given to a process in which the temperature of the alcohol of the formula II in lines (7, 8) is 10 to 30° C. and/or in which the temperature of the halosilane of the formula I in line (6) is 10 to 30° C.

Preference is given to a process in which the reaction of the compounds of the formulae I and II is conducted in a column (1) containing random packings or structured packings.

Particular preference is given to a process in which the halosilane of the formula I and a portion of the alcohol of the formula II are each introduced in the upper portion of the column (1) below the uppermost packing element (1a) and/or in which the remaining portion of the alcohol of the formula II is introduced in the lower portion of the column (1) above the lowermost packing element (1a).

The process according to the invention can be conducted at a wide range of different pressures. As well as standard pressure, procedures at elevated pressure or else under reduced pressure are possible. Preference is given to conducting the reaction of the compounds of the formulae I and II in the pressure range between 700 hPa abs and 1300 hPa abs.

The column (1) is typically heated by a circulation evaporator (3) which is mounted in the lower third of the column (1) and heats the bottom product present in the column (1).

The invention also relates to a column (1) for continuously esterifying the above-defined halosilanes of the formula I with alcohols of the formula II to give silane esters of the formula III, comprising the following elements:

A) line (6) which opens into the upper third of the column (1) and which serves to feed in the halosilane of the formula I,
B) line (7) which opens into the upper third of the column (1) and which serves to feed in a portion of the alcohol of the formula II required for the reaction,
C) line (8) which opens into the lower third of the column (1) and which serves to feed in the remaining portion of the alcohol required for the reaction,
D) circulation evaporator (3) which is mounted in the lower third of the column and heats the bottom product present in the column (1),
E) line (9) for removing the hydrogen halide formed in the reaction via the top of the column (1), and
F) line (10) for removing the process product of the formula III formed in the reaction from the bottom of the column (1).

In a preferred variant of the column (1) according to the invention, a condenser (2) is provided at the top of the column (1).

In a further preferred variant of the column (1), a product cooler (4) is provided at the lower end of the column (1) and, preferably, a pump (5) connected downstream of the product cooler (4) conveys the reaction product out of the column (1).

Figure 2:
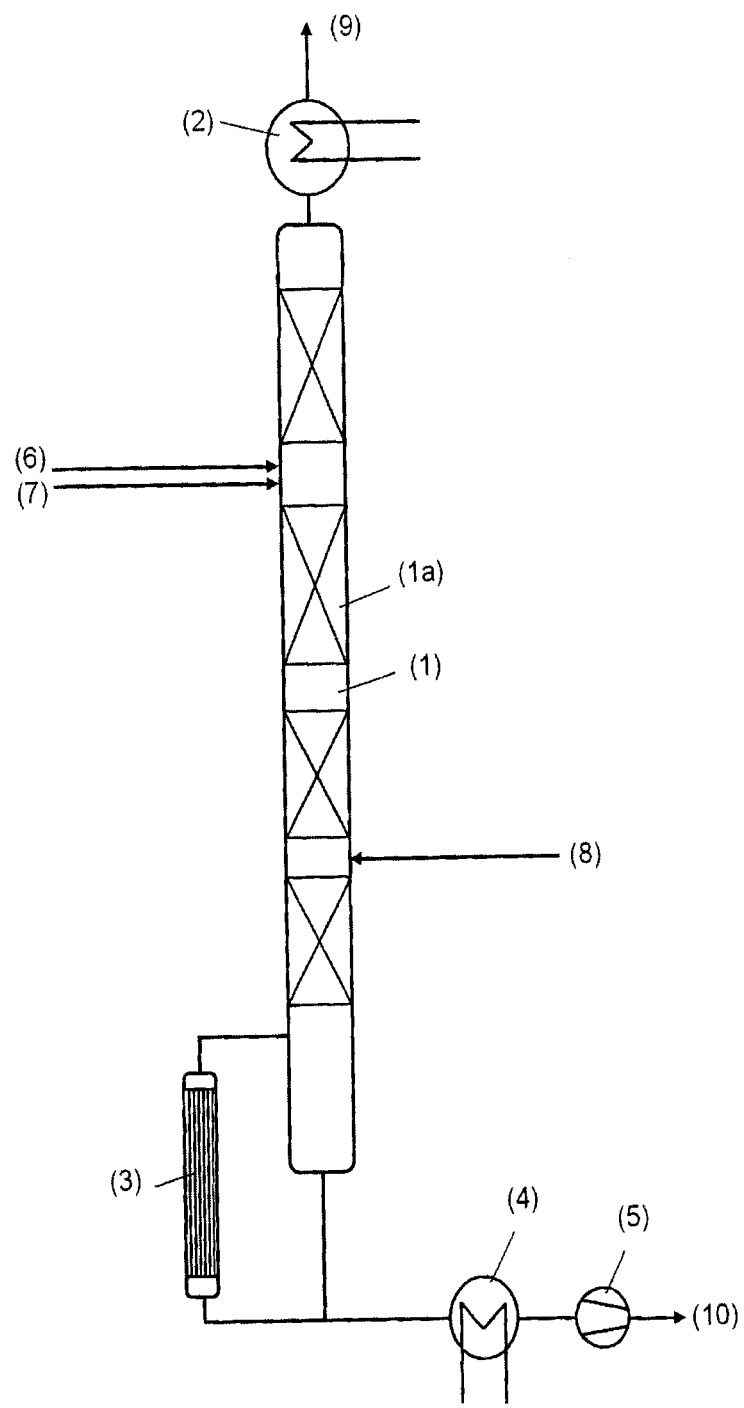

The examples which follow and FIGS. 1 and 2 give a schematic description of processes for esterification of trichlorosilane with alcohol in two series-connected columns or in one column.

EXAMPLES

Example 1 (Comparative Example)

This example describes a conventional esterification of vinyltrichlorosilane with alcohol, for example with methanol or ethanol, in two series-connected columns. The apparatus connection is shown in FIG. 1.

In a reactor column (1) equipped with top condenser (2) and circulation evaporator (3) (cf. FIG. 1), vinyltrichlorosilane and alcohol are fed in via separate lines (6, 7). These lines open into the upper third of the column, within which there are packing elements (1a). The hydrogen chloride formed in the reaction is removed via the top through line (9). Vinyltrichlorosilane and alcohol are partly converted in the reactor column (1), and the product-containing stream moves in the direction of the bottom within the column (1). Forerun column (11) is likewise equipped with packing elements (11a), top condenser (2) and circulation evaporator (3). A portion of the return stream from the forerun column (11) is recycled into the reactor column (1) via line (14). Also fed in the lower third of the forerun column (11) through line (8) is further alcohol, in order that the amount of alcohol required stoichiometrically in the overall system of reactor column (1) and forerun column (11) is present. The bottoms from reactor column (1) are cooled in the crude product cooler (4a) and conveyed by pump (5) via line (12) into the forerun column (11). Line (12) opens into the forerun column (11) in the upper third. The end product of the reaction is removed from the bottom of the forerun column (11), is cooled in the product cooler (4) and is withdrawn from the forerun column (11) by pump (5) via line (10). The circulation evaporators (3) serve to supply thermal energy for heating of the two columns (1, 11).

Example 2

This example describes an inventive esterification of vinyltrichlorosilane with alcohol, for example with methanol or ethanol, in a reaction column without using a forerun column. The apparatus connection is shown in FIG. 2.

In the upper portion of the reaction column (1) (cf. FIG. 2), vinyltrichlorosilane and the majority of alcohol are fed in via separate lines (6, 7) at the same level (but without premixing). The feed point for the two components is below the uppermost packing element (1a). In the lower portion of the column, above the lowermost packing element (1a), the remaining amount of alcohol is introduced through line (8). The reaction column (1) is operated at a slightly elevated pressure of 80 hPa. The bottom temperature is 168° C., the top temperature 40° C. A reactive distillation having 4 beds of random packings (saddles) is used; the internal diameter of the reaction column (1) is 300 mm. The mass flow rates are summarized in the following table:

| Component | Mass flow rate kg/h |
| --- | --- |
| Vinyltrichlorosilane | 300.00 |
| Alcohol line (7) | 240.00 |
| Alcohol line (8) | 13.82 |
| Vinyltriethoxysilane | 349.44 |
| Hydrogen chloride | 200.96 |
| High boilers | 3.42 |

In the bottoms from the reaction column (1), 349.44 kg/h of vinyltriethoxysilane are withdrawn. The product is cooled by product cooler (4) and discharged from the reaction column (1) via line (10) by pump (5). In the circulation evaporator (3), the amount of 160 kg/h of steam is fed in. The product heated by the circulation evaporator (3) is recycled into the reaction column (1), and serves to heat the contents of the column. At the top of the column, the mass flow rate is cooled within the top condenser (2), and 200.96 kg/h of gaseous HCl are withdrawn via line (9).

The proportion of the residue in the bottom product indicates that vinyltriethoxysilane is formed with a selectivity of 98.8%. In the two-column esterification shown in FIG. 1, in the best case a selectivity of 98.0% is arrived at in the esterification of vinyltrichlorosilane with ethanol.

Example 3

This example describes an inventive esterification of tetrachlorosilane with ethanol, in a reaction column, as described in Example 2 (FIG. 2).

In the upper portion of the reaction column (1) (cf. FIG. 2), tetrachlorosilane and the majority of ethanol are fed in via separate lines (6, 7) at the same level (but without premixing). The feed point for the two components is below the uppermost packing element (1a). In the lower portion of the column, above the lowermost packing element (1a), the remaining amount of alcohol is introduced through line (8). The reaction column (1) is operated at a slightly elevated pressure of 80 hPa. The bottom temperature is 176° C., the top temperature 38° C. A reactive distillation having 4 beds of random packings (saddles) is used; the internal diameter of the reaction column (1) is 300 mm. The mass flow rates are summarized in the following table:

| Component | Mass flow rate kg/h |
| --- | --- |
| Tetrachlorosilane | 300.00 |
| Alcohol line (7) | 305.00 |
| Alcohol line (8) | 18.65 |
| Tetraethoxysilane | 365.65 |
| Hydrogen chloride | 256.25 |
| High boilers | 1.75 |

In the bottoms from the reaction column (1), 365.65 kg/h of tetraethoxysilane are withdrawn. The product is cooled by product cooler (4) and discharged from the reaction column (1) via line (10) by pump (5). In the circulation evaporator (3), the amount of 160 kg/h of steam is fed in. The product heated by the circulation evaporator (3) is recycled into the reaction column (1), and serves to heat the contents of the column. At the top of the column, the mass flow rate is cooled within the top condenser (2), and 256.25 kg/h of gaseous HCl are withdrawn via line (9).

The proportion of the residue in the bottom product indicates that tetraethoxysilane is formed with a selectivity of 99.4%. In the two-column esterification shown in FIG. 1, in the best case a selectivity of 98.7% is arrived at in the esterification of tetrachlorosilane with ethanol.

The invention claimed is:
1. Process for continuously esterifying halosilanes of the formula I with alcohols of the formula II to give silane esters of the formula III in a single column (1)

$$R^1_a SiHal_b \quad (I)$$

$$R^2-(OH) \quad (II)$$

$$R^1_a S-(OR^2)_b \quad (III)$$

in which $R^1$ is hydrogen or a monovalent organic radical, where any two $R^1$ radicals within a molecule may be different within the scope of the given definitions, Hal is a halogen atom, a plurality of Hal atoms within a molecule may be different within the scope of the given definitions, $R^2$ is a monovalent organic radical, a and b are integers from 0 to 4 and the sum total of a and b is 4, comprising the measures of:
i) feeding the total amount of the halosilane of the formula I required for the reaction in liquid form through line (6) into the upper third of the column (1),
ii) feeding at least 60% by weight of the alcohol of the formula II required for the reaction in liquid form through line (7) into the upper third of the column (1),
iii) feeding the remainder of the alcohol of the formula II required for the reaction in liquid form through line (8) into the lower third of the column (1), iv) conducting the reaction of the halosilane of the formula I with the alcohol of the formula II to give the silane ester of the formula III in the interior of the column (1), the temperature in the interior of the column (1) between line (7) and line (8) being below the boiling temperature of the alcohol of the formula II, v) removing the hydrogen chloride formed in the reaction via the top of the column (1), and vi) removing the esterification product of the formula III formed in the reaction from the bottom of the column (1).

2. Process according to claim 1, characterized in that $R^1$ and/or $R^2$ are organic radicals selected from linear and branched alkyl, alkenyl, cycloalkyl, aryl, aralkyl and/or heterocyclyl, each of which is optionally substituted by alkyl, alkoxy, hydroxyl, amino, halogen or nitro, or in which one or more carbon atoms not directly adjacent to one another in alkyl groups are replaced by oxygen or sulphur atoms or by imino groups, or in which $R^1$ is hydrogen.

3. Process according to claim 1, characterized in that $R^1$ is hydrogen and/or $C_1$-$C_6$-alkyl and/or vinyl, especially hydrogen, methyl, ethyl or vinyl, and in that $R^2$ is $C_1$-$C_6$-alkyl, especially methyl or ethyl.

4. Process according to claim 1, characterized in that the amount of alcohol of the formula II fed in through line (7) is 70% to 95% by weight of the amount required for the reaction, and in that the remaining amount of the alcohol of the formula II required for the reaction is introduced in liquid form into the lower third of column (1) through line (8).

5. Process according to claim 1, characterized in that the compounds of the formulae I and II are introduced into the column (1) through lines (6, 7, 8) in which there are 90° bends directed vertically downward at the column ends thereof.

6. Process according to claim 1, characterized in that the temperature of the alcohol of the formula II in lines (7, 8) is 10 to 30° C.

7. Process according to claim 1, characterized in that the temperature of the halosilane of the formula I in line (6) is 10 to 30° C.

8. Process according to claim 1, characterized in that the halosilane of the formula I and a portion of the alcohol of the formula II are each introduced in the upper portion of the column (1) below the uppermost packing element (1a).

9. Process according to claim 1, characterized in that the remaining portion of the alcohol of the formula II is introduced in the lower portion of the column (1) above the lowermost packing element (1a).

10. Process according to claim 1, characterized in that the reaction of the compounds of the formulae I and II is conducted in a column (1) containing random packings or structured packings.

11. Process according to claim 1, characterized in that the reaction of the compounds of the formulae I and II is effected in the pressure range between 700 hPa abs and 1300 hPa abs.

12. Process according to claim 1, characterized in that the column (1) is heated by a circulation evaporator (3) which is mounted in the lower third of the column (1) and heats the bottom product present in the column (1).

13. Column (1) for continuously esterifying halosilanes of the formula I with alcohols of the formula II to give silane esters of the formula III according to claim 1, comprising the following elements:

A) line (6) which opens into the upper third of the column (1) and which serves to feed in the halosilane of the formula I, B) line (7) which opens into the upper third of the column (1) and which serves to feed in a portion of the alcohol of the formula II required for the reaction, C) line (8) which opens into the lower third of the column (1) and which serves to feed in the remaining portion of the alcohol required for the reaction, D) circulation evaporator (3) which is mounted in the lower third of the column and heats the bottom product present in the column (1), E) line (9) for removing the hydrogen halide formed in the reaction via the top of the column (1), and F) line (10) for removing the esterification product of the formula III formed in the reaction from the bottom of the column (1).

14. Column (1) according to claim 13, characterized in that a condenser (2) is provided at the top of the column (1).

15. Column (1) according to claim 13, characterized in that a product cooler (4) is provided at the lower end of the column (1).

16. Column (1) according to claim 15, characterized in that a pump (5) connected downstream of the product cooler (4) conveys the reaction product out of the column (1).

\* \* \* \* \*